(12) United States Patent
Kasai et al.

(10) Patent No.: US 6,800,789 B2
(45) Date of Patent: Oct. 5, 2004

(54) ABSORBENT ARTICLE

(75) Inventors: Takao Kasai, Haga-gun (JP); Megumi Kondo, Haga-gun (JP); Noriko Sato, Haga-gun (JP); Manabu Matsui, Haga-gun (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 09/852,804

(22) Filed: May 11, 2001

(65) Prior Publication Data

US 2002/0022812 A1 Feb. 21, 2002

(30) Foreign Application Priority Data

| May 12, 2000 | (JP) | 2000-140804 |
| Aug. 29, 2000 | (JP) | 2000-259823 |
| Oct. 5, 2000 | (JP) | 2000-305961 |

(51) Int. Cl.$^7$ ............................................. A61F 13/15
(52) U.S. Cl. ..................... 604/367; 604/359; 604/360; 604/364; 424/76.1
(58) Field of Search ................. 604/359, 360, 604/364, 367; 424/76.1–76.4

(56) References Cited

U.S. PATENT DOCUMENTS

| 3,814,101 A | * | 6/1974 | Kozak ........................ 604/370 |
| 4,442,125 A | * | 4/1984 | Thiele ........................ 424/318 |
| 4,556,560 A | * | 12/1985 | Buckingham ............... 424/641 |
| 5,538,728 A | * | 7/1996 | Yanaki et al. ................ 424/401 |
| 5,635,191 A | | 6/1997 | Roe et al. |
| 5,643,588 A | * | 7/1997 | Roe et al. .................... 424/402 |
| 5,648,083 A | * | 7/1997 | Blieszner et al. ........... 424/402 |
| 5,865,822 A | * | 2/1999 | Hamajima et al. .......... 604/367 |
| 5,871,763 A | * | 2/1999 | Luu et al. .................... 424/402 |
| 5,968,025 A | * | 10/1999 | Roe et al. .................... 604/364 |
| 6,217,889 B1 | * | 4/2001 | Lorenzi et al. .............. 424/401 |
| 6,217,890 B1 | * | 4/2001 | Paul et al. ................... 424/402 |
| 6,287,582 B1 | * | 9/2001 | Gott et al. ................... 424/402 |

FOREIGN PATENT DOCUMENTS

| JP | 860547 | 3/1996 |
| JP | 3048431 | 6/2000 |
| WO | WO9616681 | 6/1996 |
| WO | WO9616682 | 6/1996 |
| WO | WO 98/24390 | 6/1998 |
| WO | WO 99/45973 | 9/1999 |

OTHER PUBLICATIONS

Patent Abstract of Japan, JP09 071527, Mar. 18, 1997.
Patent Abstract of Japan, JP04 069329, Mar. 4, 1992.
Abstract of Korean patent, KR9 615 184, Nov. 1, 1996.

* cited by examiner

Primary Examiner—John J. Calvert
Assistant Examiner—Jacqueline F. Stephens
(74) Attorney, Agent, or Firm—Birch, Stewart, Kolasch & Birch, LLP (57) ABSTRACT

An absorbent article comprising a liquid retentive absorbent layer containing a superabsorbent polymer and a liquid-impermeable leak proof layer is disclosed. An agent having a skin care effect and substantially no decomposing action on the superabsorbent polymer is fixed on a prescribed region of the absorbent article in a state ready to be released from that region upon contact with moisture.

10 Claims, 1 Drawing Sheet

Fig. 1

ABSORBENT ARTICLE

BACKGROUND OF THE INVENTION

The present invention relates to an absorbent article containing a superabsorbent polymer, which effectively prevents skin rash development without reducing the absorbing performance of the superabsorbent polymer. The present invention also relates to an absorbent article having an agent which has hardly been subjected to thermal history and by which scratches, rashes or inflammation of wearer' skin can be suppressed or cured. The present invention also relates to fiber or a fiber aggregate having skin-care effects and suitable for use in these absorbent articles.

Absorbent articles developed for preventing rash development on wearer's skin include those disclosed in WO96/16681 and WO96/16682. These publications show disposable diapers having a lotion containing an emollient applied to the topsheet. The lotion used contains an immobilizing agent for fixing the emollient to the topsheet.

Immobilized on the topsheet, the emollient hardly migrates to the wearer's skin so that not all the emollient applied to the topsheet participates in antiinflammation. Some immobilizing agents used for fixing the emollient irritate the skin to produce a rash. The lotion sometimes gets hard to cause small scratches on the skin, which can also result in a rash.

In producing the above-described disposable diapers, the emollient is melted together with the immobilizing agent, and the molten mixture is applied to a topsheet. That is, the emollient is repeatedly exposed to high temperature for a long time (thermal history) and, as a result, often undergoes thermal denaturation or thermal decomposition. The immobilizing agent itself and the emollient in the presence of the immobilizing agent tend to become hard to scratch the skin. These agents are difficult to apply uniformly, which is a false economy.

Further, the disclosed disposable diapers are liable to leak because the immobilizing agent used is hydrophobic so that liquid waste discharged on the topsheet is not allowed to quickly permeate through the topsheet, rather tending to flow thereon. In order to secure smooth permeation of liquid, the amount of the lotion applied should be reduced, or application of the lotion must be discontinuous, but such manipulations will ruin the effects that should have been produced. In addition, the area in the topsheet where the lotion is applied interferes with smooth permeation of the liquid waste, resulting in remaining the liquid waste on the topsheet. The liquid waste remained on the topsheet causes swell of the wearer's skin which leads to unfavorable skin rash due to, for example, scratch and infection of irritating substances.

There are some other known absorbent articles having a pharmacologically active ingredient to prevent a rash. However, without a proper choice of the active ingredient, the crosslinked structure of a superabsorbent polymer would be severed by the active ingredient to reduce liquid absorptivity and increase a back-flow. An increased back-flow brings skin overhydration, which accelerates a skin rash. A reduction in amount of the active ingredient only leads to a failure to exert the anti-rash effect.

Apart from the absorbent articles disclosed in the above publications, fibers having adhered thereto a skin-care agent have been proposed. Japanese Patent Laid-Open 5-44165 discloses chitosan-containing fiber, and Japanese Patent Laid-Open 8-60547 proposes sericin-containing fiber.

Chitosan and sericin generally have high crystallinity and low water solubility and are therefore not easy to apply in fiber processing. Specifically, chitosan or sericin precipitates and falls off while being adhered to fibers. As a result, the production equipment is soiled, and the resulting fiber has an insufficient add-on, and the adhesion is not uniform. A manipulation for increasing the add-on could result in more precipitation and fall-off, making a vicious circle.

Accordingly, an object of the present invention is to provide an absorbent article containing a superabsorbent polymer, which effectively prevents rash development without reducing the absorbing performance of the superabsorbent polymer.

Another object of the present invention is to provide an absorbent article having an agent fixed thereto with reduced involvement of thermal history so that the agent keeps effective in suppressing or curing scratches, a rash or inflammation of wearer' skin.

Still another object of the invention is to provide an absorbent article which prevents discharged liquid waste from flowing on the skin-contacting surface thereof.

Yet another object of the invention is to provide an absorbent article containing an agent effective on the skin which exhibits improved stability while dry and manifests sufficient performance while worn.

A further object of the invention is to provide skin-care agent-containing fiber the skin-care agent of which has high water solubility to produce sufficiently high skin care effects.

A furthermore object of the invention is to provide skin-care agent-containing fiber having high skin care effects which can be produced by a simple process.

SUMMARY OF THE INVENTION

To accomplish the above objects, the present invention provides, in its first aspect, an absorbent article comprising a liquid retentive absorbent layer containing a superabsorbent polymer and a liquid-impermeable leak proof layer, wherein an agent having a skin care effect and substantially no decomposing action on the superabsorbent polymer is fixed on a prescribed region of the absorbent article in a state ready to be released from that region on contact with moisture.

The present invention also provides, in its second aspect, skin-care agent-containing fiber comprising fiber and an effective amount of a skin-care agent fixed on the fiber in a state ready to be released on contact with moisture.

The present invention also provides, in its third aspect, an absorbent article comprising a liquid retentive absorbent layer and a liquid-impermeable leak proof layer, wherein an agent having a prescribed effect on the skin of a wearer is fixed with a water-soluble thickener on a prescribed region of the absorbent article.

DETAILED DESCRIPTION OF THE PREFERRED EMBODIMENTS

Figure 1:
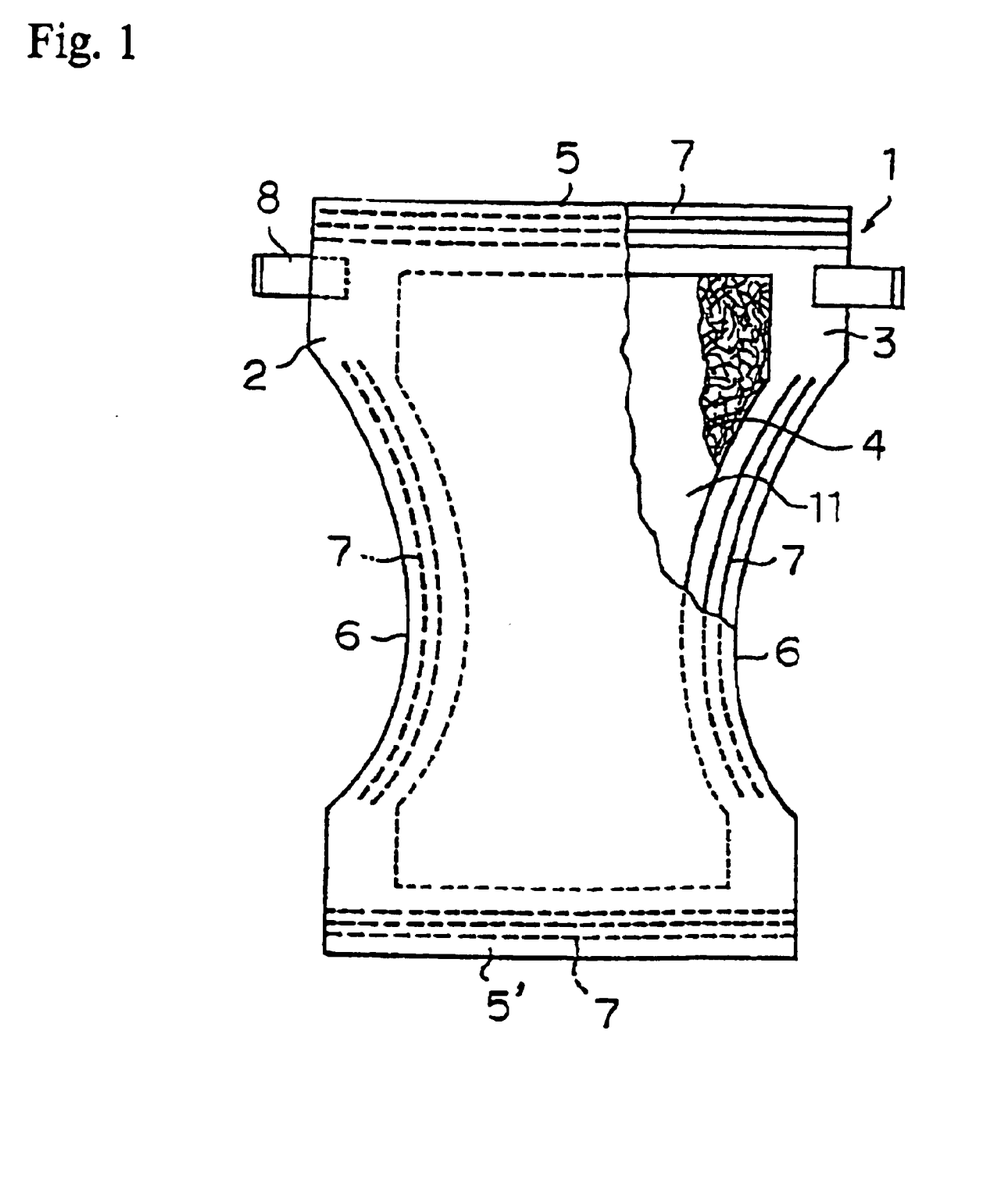
FIG. 1 is a plan view of a disposable diaper as an embodiment of the absorbent article according to the present invention, with a part being cut away, seen from its topsheet side.

The first aspect of the present invention will be described with particular reference to a disposable diaper as a preferred embodiment and to the accompanying drawing. As shown in FIG. 1, the disposable diaper 1 according to this embodiment comprises a topsheet 2 (e.g., nonwoven fabric or perforated film) which serves as a liquid-permeable top layer, a backsheet 3 (e.g., a thermoplastic resin sheet) which serves as a liquid-impermeable leak proof layer, and an absorbent member 4 interposed between the topsheet 2 and the backsheet 3 and serving as a liquid retentive absorbent layer. The absorbent member 4 has its portion corresponding to the crotch portion of the diaper 1 narrowed to have the shape of a sandglass. The topsheet 2 and the backsheet 3 are also shaped into a sandglass similar to the absorbent member 4. The absorbent member 4 is fixedly held in between the topsheet 2 and the backsheet 3.

The topsheet 2 and the backsheet 3 extend outward from the front and the rear ends and the lateral sides of the absorbent member 4 to form a front and a rear waist portion 5' and 5 and a pair of leg portions 6 and 6. The front and the rear waist portions 5' and 5 and the pair of leg portions 6 and 6 are each provided with elastically stretchable members 7 for giving the waist portions 5 and 5' and the leg portions 6 and 6 a good fit to a wearer's body when put on the wearer. The stretchable members 7 are fixed by the topsheet 2 and the backsheet 3. A pair of fastening members 8, such as sets of tape fasteners, are attached to both lateral sides of the rear waist portion 5. While not shown, a mating member, such as a rectangular landing tape, is provided on the backsheet 3 in the front waist portion 5'. On putting the disposable diaper 1 of the embodiment on a wearer, the fastening members 8 are stuck on this mating member. The above-mentioned constitution and structure are the same as in conventional disposable diapers.

The absorbent member 4 comprises nonwoven fabric and superabsorbent polymer particles held among interstices of the constituent fibers of the fabric. The nonwoven fabric having the superabsorbent polymer particles is enveloped in tissue 11 to make the absorbent member 4. The absorbent member 4 having such a structure is extremely thin as compared with conventional absorbent members which are made mainly of pulp and superabsorbent polymer particles. The fiber fabricating the nonwoven fabric includes hydrophilic fibers such as rayon, cotton and cellulose acetate; polyolefin fibers such as polyethylene and polypropylene; condensation fibers such as polyester and polyamide; and vinyl polymeric fibers such as polyvinyl chloride and polyvinyl acetate. Hydrophobic fibers can previously be rendered hydrophilic by treatment with textile oils, etc.

The superabsorbent polymer which can be used in the present invention preferably has a physiological saline absorption of 30 g/g or more, particularly 30 to 50 g/g, especially 35 to 50 g/g, as measured by a centrifugal dewatering method (hereinafter referred to as "a water absorption by centrifugal dewatering" or simply "a water absorption"). A superabsorbent polymer having a water absorption of less than 30 g/g would have to be used in an increased proportion in the absorbent member 4 to secure sufficient absorptivity, which is not only a false economy but makes the diaper bulky and less portable. The above-identified water absorption is measured as follows.

Method of Measuring Water Absorption by Centrifugal Dewatering

A superabsorbent polymer weighing 1 g is swollen with 150 ml of physiological saline for 30 minutes and put into a nylon mesh (250 mesh) bag. The bag containing the swollen polymer is dewatered by centrifugation at 143 G (800 rpm) for 10 minutes and then weighed. The water absorption (g/g) is calculated according to equation (1):

Water absorption by centrifugal dewatering=[(total weight after centrifugation)−(weight of nylon mesh bag)−(weight of superabsorbent polymer)−(weight of liquid attached to nylon mesh bag)]/(weight of superabsorbent polymer)  (1)

The superabsorbent polymer which can be used in the present invention is not particularly limited as long as a desired absorbing function is performed. Suitable superabsorbent polymers include sodium polyacrylate, (acrylic acid-vinyl alcohol) copolymers, crosslinked sodium polyacrylate, (starch-acrylic acid) graft polymers, (isobutylene-maleic anhydride) copolymers and saponification products thereof, potassium polyacrylate, and cesium polyacrylate. The above-described preferred absorption performance can be obtained by, for example, providing the surface of the polymer particles with a gradient of crosslinking density or producing the polymer as non-spherical amorphous particles. Specifically, the technique described in the U.S. Pat. No. 5,865,822, column 10, line 62 to column 12, line 40 can be used, which is incorporated herein by reference.

In order to prevent development of gel blocking phenomenon and resultant reduction in absorbing performance and to prevent liquid from flowing and leaking due to slow absorption, it is preferred for the superabsorbent polymer to have a liquid passage time of 20 seconds or shorter, particularly 2 to 15 seconds, as measured as follows.

Method of Measuring Liquid Passage Time

A superabsorbent polymer weighing 0.5 g is put in a cylinder having a crosssectional area of 4.91 cm$^2$ (inner diameter: 25 mm) with the bottom closed with a cock (inner diameter: 4 mm) together with physiological saline to let the polymer be swollen with saline to saturation. After the swollen superabsorbent polymer has sunk, the cock is opened to let the physiological saline pass through the polymer. The time required for 50 ml of the saline to pass is taken as a liquid passage time.

The superabsorbent polymer is preferably used in an amount of 5 to 300 g/m$^2$, particularly 100 to 250 g/m$^2$. More than 300 g/m$^2$ of the superabsorbent polymer tends to move due to insufficient entanglement with the nonwoven fabric, which leads to instable absorbing performance.

The diaper 1 according to the present embodiment has an agent applied to the topsheet 2, the skin-contacting surface. The agent has a skin care effect to the skin of a wearer. The term "skin care effect(s)" as used herein encompasses any skin care effects for normalizing the wearer's skin, such as a rash preventive effect, an antiinflammatory effect, a scratch preventive effect, an astringent effect and an antimicrobial effect. The agent having a skin care effect(s) is often referred to as a "skin-care agent" throughout the specification. The skin-care agent used in the present embodiment should have substantially no decomposing action on the superabsorbent polymer contained in the absorbent member 4. The language "substantially no decomposing action on a superabsorbent polymer" includes cases where the agent has no decomposing action on a superabsorbent polymer and cases where the agent has such a low decomposing action on a superabsorbent polymer not to cause substantial reduction of the water absorbing performance of the superabsorbent polymer. With the skin-care agent applied, the diaper 1 is effective in protecting the wearer's skin against rash development or inflammation due to contact with body exudates such as urine or sweat, and in curing in case such a skin disorder develops. The superabsorbent polymer present in the absorbent member 4 is prevented from decomposition and resultant reduction in absorbing performance. To prevent decomposition of the superabsorbent polymer is especially beneficial where the superabsorbent polymer has a large absorption capacity (a high water absorption by centrifugal dewatering) as in the case of the absorbent member 4 used in the present embodiment.

The skin-care agent is fixed on the topsheet 2 in a state ready to be released from the topsheet 2 on contact with moisture. The manner of fixing the skin-care agent is preferably such that the agent leaves the topsheet 2 on contact with a water content, typically a body fluid such as urine and perspiration, diffuses and dissolves in the body fluid, whereby the agent becomes movable and ready to reach the wearer's skin and adhere thereto. As a result, the skin is prevented from developing a diaper rash or inflammation, or, if such a skin disorder happens, it can be cured rapidly.

The language "fixed in a state ready to be released on contact with moisture" as used herein means that the skin-care agent has sufficiently high solubility or dispersibility in water. For example, a skin-care agent fixed on a topsheet 2 "in a state ready to be released on contact with moisture" is completely dissolved or dispersed in water when the topsheet 2 is soaked in 10 times as much water as its own weight at 25° C. The skin-care agent may migrate and reach the wearer's skin by the aid of additional means together with moisture, as far as the skin-care agent can migrate and reach the wearer's skin upon contact with moisture.

The above-described state of fixing can be achieved by, for example, using a nonwoven fabric as a topsheet 2 in which constituent fibers are previously treated with the skin-care agent. In this case, the skin-care agent is mixed into an aqueous solution of a textile oil (e.g., a surface active agent), and the mixture is applied to the fiber. The details of such skin-care agent-containing fiber will be discussed later in terms of the second aspect of the present invention.

The above-described state of fixing can also be obtained by applying the skin-care agent directly on the topsheet 2. The skin-care agent is mixed with a surface active agent and, if desired, a penetration accelerator hereinafter described, and the resulting mixture is applied to the topsheet 2.

The skin-care agents include extracts of various plants, ceramides (including natural ceramides and pseudoceramides), collagen, humectants such as squalane, squalene, natural moisturizing factor (NMF), 1,3-butylene glycol, propylene glycol and glycerol, keratin softeners such as arginine and guanidine derivatives (e.g., salts of 2-(2-hydroxyethoxy)ethylgluanidine with organic acids, e.g., succinic acid, glycolic acid, lactic acid, malic acid, citric acid and tartaric acid), and antiinflammatory agents such as guaiazulene, tannin, gallic acid derivatives and bisabolol. From the standpoint of water solubility, skin care effects and cost, plant extracts, ceramides and NMF are preferred. Pseudoceramides are preferred to natural ceramides because the latter are difficult to extract, expensive and labile. Pseudoceramides include water-retaining ceramides and barrier ceramides.

The plant extract is obtainable by grinding a whole plant or one or more of plant parts (e.g., leaves, bark, roots, branches, etc.), either dried or undried, and extracting with a solvent at ambient temperature or under heating or by means of an extractor, e.g., a Soxhlet's extractor. Any plant extract can be used with no particular restriction as long as it has a skin care effect and substantially no decomposing action on superabsorbent polymers. Examples of suitable plant extracts are oat extract, alga (e.g., bladder wrack (*Fucus vesiculosis*)) extract, citron extract, hamamelis extract, burnet extract, hiba arborvitae extract, aloe extract, phellodendron extract, field horsetail extract, chamomile extract, eucalyptus extract, and peach leave extract. Of these plant extracts one or more agents selected from the group consisting of citron extract, hamamelis extract, hiba arborvitae extract, aloe extract, phellodendron extract and peach leave extract provide enhanced skin care effects and enhanced prevention of superabsorbent polymer decomposition. In particular, citron extract, hamamelis extract and hiba arborvitae extract are preferred for their effects in favor of the skin and the superabsorbent polymer. It is preferred that the plant extract be a 1,3-butylene glycol extract because of its higher water solubility and no need to take an explosion-proof measure in a heat treatment involved in the manufacture of absorbent articles. Additionally the 1,3-butylene glycol extract will leave 1,3-butylene glycol in the diaper 1 together with the plant extract to reduce deterioration of absorbing performance.

A plant extract as obtained usually contains an extracting solvent and water in addition to the active ingredients. A sufficient active ingredients concentration in the extract as obtained (i.e., the resulting concentration in which water and volatile solvents are removed from the extract as obtained) is 0.001 to 5% by weight. In particular, where 1,3-butylene glycol is used as an extracting solvent, it is preferred that the total concentration of the active ingredients and 1,3-butylene glycol is within the above range. A preferred concentration of the active ingredients is 0.001 to 10% by weight based on the solvent.

The pseudoceramides preferably include water-retaining ceramides or barrier ceramides which are represented by formulae shown below.

Water-retaining Ceramide wherein $R_1$ and $R_2$, which may be the same or different, each represent an alkyl group having 12 to 40 carbon atoms.

Water-retaining Ceramide wherein $R_6$ and $R_9$, which may be the same or different, each represent an alkyl group having 12 to 40 carbon atoms; $R_7$ represents a hydrogen atom, a methyl group or an ethyl group; $R_8$ represents a hydrogen atom, a methyl group, an ethyl group or a group of formula:

and p represents an integer of 1 to 6.

Barrier Ceramide wherein $R_3$ and $R_5$, which may be the same or different, each represent an alkyl group having 12 to 40 carbon atoms; and $R_4$ represents an alkylene group having 12 to 40 carbon atoms.

Barrier Ceramide wherein $R_{10}$ and $R_{11}$, which may be the same or different, each represent an alkylene group having 5 to 18 carbon atoms; and $R_{12}$ and $R_{13}$, which may be the same or different, each represent an alkyl group having 3 to 12 carbon atoms.

The skin suffering from scratches caused by rubbing with the topsheet 2 can easily develop a rash in the presence of even a slight amount of an irritant. Therefore, the topsheet 2 is preferably made of a web of a soft fiber aggregate, such as nonwoven or woven fabric. The thickness of fibers constituting the fiber aggregate is preferably 0.5 to 8.9 dtex, still preferably 1 to 5.6 dtex.

When nonwoven fabric is used as the topsheet 2, it is desirable that the fiber be heat treated at a temperature higher than its melting point by 10° C. at the highest to make nonwoven fabric with improved softness. In this case, however, the resulting nonwoven fabric may have insufficient strength for the manufacture of diapers or for practical use of the diapers. It is therefore recommended to carry out embossing to improve the fabric strength and also to raise the level of the skin-contacting surface thereby accelerating transfer of the skin-care agent to the skin. Embossing of the nonwoven fabric is preferably such as to achieve an embossed area ratio of 5 to 50%, particularly 10 to 30%, in the light of improvement on nonwoven fabric strength, prevention of reduction in texture, and prevention of stickiness that can develop if the level of the skin-contacting surface is too much raised.

Where nonwoven fabric is used as the topsheet 2, it is preferred that a considerable quantity of the skin-care agent be applied on the skin-contacting side of the nonwoven fabric so that the agent may be transferred to the skin effectively. Such a manner of applying the skin-care agent is preferably embodied by using multi-layered air-through nonwoven fabric having at least two layers in which the uppermost layer, i.e., the skin-contacting layer has an increased amount of the skin-care agent. It may follow that the upper layer with a decreased proportion of the hydrophilic textile oil exhibits reduced absorbing performance. To avoid this, it is preferable to make up the lower layer, i.e., the layer which is not brought into contact with the skin, of fibers having a relatively large thickness and to make up the upper layer (the skin-contacting layer) of conjugate fibers having a relatively small thickness. Conjugate fibers, such as side-by-side type ones and eccentric core/sheath type ones, can be crimped to provide larger spaces among themselves for their small thickness (small fiber thickness secures a soft texture) to have an improved absorption rate. For the same purpose, thermally shrinkable fiber can be used as part of the upper layer.

The skin-care agent is applied to at least the main absorbing region of the topsheet 2. The term "main absorbing region" indicates the region covering the crotch portion and extending therefrom toward the front and the rear waist edges except the peripheral area of the topsheet 2. As a matter of course, the skin-care agent can be applied to the entire area of the topsheet 2. The skin-care agent can be applied either solid or with spacing, for example, in a pattern of stripes. The skin-case agent can also be applied to any other parts that are brought into contact with the wearer's skin, such as the cuffs (upstanding guards against liquid flow), leg portions, the portion around the waist, and the like.

From the viewpoint of safety/effect balance and economies, the amount of the skin-care agent to be applied to the main absorbing region preferably ranges from 0.005 to 3%, particularly 0.05 to 1%, by weight based on the weight of that region of the topsheet 2, while somewhat varying depending on the extraction method or the extracting solvent.

A penetration accelerator which accelerates penetration of the skin-care agent into the skin can be applied to the region where the skin-care agent is applied. A penetration accelerator is effective in further suppressing development of a rash or inflammation and accelerating curing of such a skin disorder if it develops.

The penetration accelerator preferably has a solubility parameter of 15 to 17, particularly 16 to 16.8, so that the diaper can retain a dry and non-sticky feel.

Aliphatic ethers or aliphatic esters are preferred penetration accelerators. Because a process of manufacturing absorbent articles usually involves heat application to join constituent members, aliphatic ethers which are thermally stable and hardly susceptible to thermal denaturation or decomposition are particularly preferred.

Preferred examples of the aliphatic ethers as a penetration accelerator include myristyl 1,3-dimethylbutyl ether, palmityl 1,3-dimethylbutyl ether, stearyl 1,3-dimethylbutyl ether, palmityl 3-methylpropyl ether, and stearyl 3-methylpropyl ether.

In addition to the penetration accelerator, other components, such as a penetration accelerator gelling agent, can be applied to the region where the skin-care agent is applied. Cases are sometimes met with in which the penetration accelerator impairs the absorbing performance of the superabsorbent polymer of the absorbent member 4. In such cases, the gelling agent will gel the penetration accelerator to moderately control the diffusion of the penetration accelerator into the superabsorbent polymer, thereby to effectively avoid the adverse influence of the penetration accelerator on the superabsorbent polymer.

The gelling agent include agents capable of controlling diffusion and migration of the penetration accelerator, such as paraffin wax, $C_{12}$–$C_{22}$ fatty acids, $C_{12}$–$C_{22}$ aliphatic alcohols, vaseline, sorbitan mono-, di- or tri-fatty acid esters, and polyoxyethylene sorbitan fatty acid esters.

The gelling agent is preferably applied in an amount of 10 to 200 parts by weight, particularly 50 to 100 parts by weight, per 100 parts by weight of the penetration accelerator, from the standpoint of economies, feel, and processability.

Still other components that can be applied to the region where the skin-care agent is applied include viscosity modifiers for adjusting the viscosity of a mixture to be applied which contains the skin-care agent and, if desired, the penetration accelerator and, if desired, the gelling agent. Useful viscosity modifiers include liquid paraffin, silicone oil, animal or vegetable oils (e.g., squalane, olive oil, jojoba oil, and safflower oil), and mono-, di- or triglycerides. It is desirable for a mixture comprising the aforementioned skin-care agent, penetration accelerator, gelling agent, and viscosity modifier to have a JIS hardness of 20 to 50 at room temperature (20° C.) for securing both transfer of the skin-care agent and the feel of the skin-contacting side.

For the purpose of smoothing or drying the skin, organic or inorganic particles, such as zinc white, talc, titanium oxide, silicone beads and nylon beads, can be applied to the region having the skin-care agent. These particles preferably have a particle diameter of 0.05 to 50 µm, particularly 1 to 20 µm, to accomplish the purpose.

In another preferred embodiment of the diaper 1, the skin-care agent is fixed with a water-soluble thickener thereby to ensure hold of the skin-care agent before use and to effectively release the skin-care agent during use. The details of the water-soluble thickener and its usage will be discussed later with respect to the third aspect of the invention.

Next, the skin-care agent-containing fiber according to the second aspect of the present invention will be described. The skin-care agent-containing fiber is suited for use as the topsheet 2 of the above-described disposable diaper 1. It is fiber having the above-described skin-care agent fixedly adhered to the surface thereof The skin-care agent is adhered in a state ready to release upon contact with moisture. The skin-care agent is adhered in an effective amount enough to exhibit desired skin care effects. The amount of the skin-care agent to be adhered is dependent on the kind of the agent. With the skin-care agent applied being the same, the skin-care agent-containing fiber of the present invention exhibits equal skin care performance with a smaller skin-care agent content as compared with conventional skin-care agent-containing fibers. The skin-care agent could be applied in an increased amount, but because the skin care effects are eventually saturated, the upper limit of the amount to be applied should be decided from the balance between the skin care effects exerted and economies.

Specifically, in using a plant extract as a skin-care agent, the amount of the skin-care agent is about 0.01 to 5%, particularly about 0.05 to 2%, by weight based on the weight of the skin-care agent-containing fiber.

The skin-care agent is adhered to the fiber surface either continuously or discontinuously in the form of, for example, particles or film. The film of the skin-care agent may be a continuous film or a discontinuous film.

In order to fix the skin-care agent on the fiber surface in a state ready to be released therefrom on contact with moisture, it has been found effective to adhere the skin-care agent (i.e., the skin-care agent other than 1,3-butylene glycol) together with a textile oil or 1,3-butylene glycol. A combined use of a textile oil and 1,3-butylene glycol was found particularly effective. It is preferred to use 1,3-butylene glycol as a solvent for the skin-care agent. The reason has been described previously. Additionally, 1,3-butylene glycol is used as skin-care agent itself, as previously stated.

Adhesion of the skin-care agent to the fiber surface together with a textile oil is preferably effected by applying a mixture comprising the skin-care agent and the textile oil and, if desired, 1,3-butylene glycol to the surface of the fiber followed by drying. Where 1,3-butylene glycol is employed, other materials than 1,3-butylene glycol are used as skin-care agent. Specifically, a method comprising soaking the fiber in the mixture, taking the fiber out of the mixture, and drying the impregnated fiber by a prescribed means is preferred for its simplicity and ease. A method comprising spraying the mixture to the fiber and drying the fiber by a prescribed means is also preferred for the same reason.

The textile oil encompasses so-called finishing lubricants used in the manufacture of fiber. The textile oil to be used preferably includes surface active agents, such as anionic surface active agents, cationic surface active agents, and nonionic surface active agents. Specific examples of suitable surface active agents are polyoxyalkylsulfuric ester metal salts, alkylsulfuric ester metal salts, polyoxyethylene alkylphosphate metal salts, alkylphosphate metal salts, fatty acid diethanolamides, sorbitan mono-, di- or tri-fatty acid esters, alkyl glucosides, polyglycerol fatty acid esters, alkylsuccinate metal salts, and higher alcohols. The metal salts include sodium salts and potassium salts. These surface active agents can be used either individually or as a combination of two or more thereof. From the viewpoint of hydrophilic properties, capability of repeatedly absorbing liquid, anticorrosion, and fabricability into nonwoven fabric, polyoxyethylene alkylphosphate metal salts, alkylphosphate metal salts, fatty acid diethanolamides, sorbitan fatty acid esters, alkyl glucosides, alkylsuccinate metal salts, and their combinations are preferred.

The textile oil can contain additives, such as antistatics, antioxidants, pH adjusting agents, smoothing agents, emulsifiers, antibacterial agents, antifungal agents, perfumes, and so forth.

In addition to the skin-care agent, an anti-frictional agent can be adhered to the fiber for the purpose of reducing scratches on the skin. Useful anti-frictional agents include plate-like crystals of organic agents, such as acylated taurine metal salts (e.g., calcium lauroyltaurinate and calcium lauroyl-β-alanyltaurinate), distearyl ether, sodium zinc cetylphosphate, N-ε-lauroyl-L-lysine, and organic particles (e.g., silicone beads, nylon beads, and chitosan beads).

The fiber to which the skin-care agent is to be adhered includes natural fibers, such as pulp and cotton; semi-synthetic fibers, such as rayon and Tencel (RTM), and synthetic fibers comprising thermoplastic resins, such as polyethylene, polypropylene, polyethylene terephthalate, polyacrylic acid, and polyamide. Conjugate fibers composed of the thermoplastic resins, such as core/sheath type ones and side-by-side type ones, are also useful. These fibers can be used either individually or as a combination thereof The fiber may be either long fiber filament or staple fiber.

The fiber thickness is not particularly limited and can be selected appropriately according to the use. For example, the skin-care agent-containing fiber for preparing the topsheet of an absorbent article preferably has a fiber diameter of 0.5 to 8.9 dtex, particularly 1 to 5.6 dtex, as previously noted with respect to the first aspect of the present invention in view of the texture, liquid permeability, hiding properties, strength, etc. of the topsheet.

In the second aspect of the invention, a fiber aggregate comprising the above-described skin-care agent-containing fiber is also provided. Such a fiber aggregate includes nonwoven fabric of various types, woven fabric, paper, and textile. The fiber aggregate is preferably used as a member that comes into direct or indirect contact with a user's skin and exhibits desired skin care effects to the skin of a wearer. For instance, as stated with reference to the first aspect of the invention, nonwoven fabric as a fiber aggregate can be used as a topsheet of an absorbent article to produce effects in suppressing a skin rash or inflammation or curing a skin rash or inflammation rapidly. In this application the skin-care agent releases from the fiber on contact with moisture, typically body fluids such as urine and perspiration, diffuses and dissolves in the body fluids and easily migrates to the wearer's skin to exert its skin care effects.

Although a sheet coated with a skin-care substance is known as a pack for skin treatment, it does not possess air permeability nor moisture permeability. To the contrary, fibrous products comprising the fiber aggregate made of the skin-care agent-containing fiber exhibit air permeability and moisture permeability as well as skin care effects. A fiber product comprising the skin-care agent-containing fibers and water or a cosmetic lotion can be a suitable pack for skin treatment due to its improved air permeability. In addition, the skin-care agent-containing fiber can be fabricated into fibrous articles which are to be worn for a long time, such as socks, underwear, and gloves. Such fibrous articles will prevent overhydration of the skin while producing prescribed skin care effects during long-term use.

The third aspect of the present invention will then be described, similarly to the first aspect of the invention, with particular reference to the disposable diaper shown in FIG. 1 as a preferred embodiment. Unless otherwise described, the description which has been given with respect to the first and second aspects of the invention applies to the common part of the third aspect. In this embodiment, an agent having a prescribed effect on the skin of a wearer is fixed and held to the skin-contacting surface, specifically the topsheet 2, by means of a water-soluble thickener. The agent is applied by coating the topsheet 2 with an aqueous solution or dispersion containing the agent and the water-soluble thickener, followed by drying preferably at a temperature of from room temperature up to 150° C. The heat of drying is absorbed by the water content of the aqueous solution or dispersion, which effectively prevents the agent from thermal denaturation or decomposition. In other words, the agent can be applied to the topsheet 2 without undergoing thermal history so that the agent can fully manifest its effect in reducing and/or curing scratches, a rash and inflammation of the wearer's skin.

The agents which can be used in the third aspect of the invention are not particularly limited as long as they exert a prescribed effect on the wearer's skin. Useful agents having a prescribed effect on the wearer's skin include the following three groups of substances.

(1) Skin-care agents, which are the same as those described with respect to the first and the second aspects.

(2) Cosmetically acceptable oils, such as isopropyl myristate, isopropylpropanol, vaseline, cetanol, stearyl alcohol, and glycerol tri(2-ethylhexanoate).

(3) Organic or inorganic particles which adhere to the skin to reduce friction or to make the skin smooth thereby serving to protect the skin from being scratched, such as silicone beads, nylon beads, zinc white, chitosan beads, silk powder, N-ϵ-lauroyl-L-lysine, sodium cetylphosphate, and calcium lauroyltaurinate. The particles preferably have a particle diameter of 0.05 to 50 $\mu$m, particularly 1 to 20 $\mu$m, for avoiding scratching the skin.

The emollients described in WO96/16681 and WO96/16682 supra are also useful as a agent having a prescribed effect on the skin.

The above-described agents can be used either individually or as a combination of two or more thereof.

Of the above agents those soluble or dispersible in water are preferred for miscibility with the water-soluble thickener. In using agents that are not soluble nor dispersible in water, for example, hydrophobic agents, an appropriately selected surfactant can be used in combination to improve water dispersibility of the agent.

The water-soluble thickener which can be used in the present invention includes polyhydric alcohols such as gylcerol, 1,3-butylene glycol and dipropylene glycol, polyvinyl alcohol, carboxyalkyl cellulose, and thickening polysaccharides. These water-soluble thickeners can be used either individually or as a combination of two or more thereof. By the action of the water-soluble thickener, the agent is stably fixed to a predetermined region of the diaper. Being water-soluble, the thickener allows the agent to be formulated into an aqueous solution or dispersion and be applied to a predetermined region of the diaper without being subjected to thermal history. Thus, the agent maintains its effects. For the thickener to be water-soluble has another advantage that a fear of a discharged body fluid's leaking is eliminated because the liquid quickly permeates and diffuses into the absorbent member 4 without flowing on the surface of the topsheet 2. Still another advantage of the water-soluble thickener is that it easily dissolves in a discharged body fluid to release the agent having been fixed and to let the agent reach and adhere to the wearer's skin.

For ease of fixing the agent and processability and storage stability of the agent, the water-soluble thickener preferably has a water dissolving temperature of 40 to 100° C., particularly 60 to 80° C., as measured in accordance with the following method.

Method of Measuring Water Dissolving Temperature

A uniform mixture of 20 parts by weight of a water-soluble thickener and 100 parts by weight of water is cast on a glass plate and dried into film. A 5 mm-wide strip cut out of the resulting film is attached to an angular U-shaped holder and immersed in water. The water temperature is raised slowly while observing the state of the film strip with the naked eye. The temperature at which the film strip is dissolved and cut is a water dissolving temperature.

The polyvinyl alcohol used as the water-soluble thickener preferably has a degree of saponification of more than 85%, particularly more than 95%, and a degree of polymerization of 1000 to 3000, particularly 1500 to 2500. Within these ranges, the polyvinyl alcohol has improved processability and holding properties for the agent while dry and, on contact with water, exhibits improved releasability for the fixed agent. The above ranges are also preferred from the standpoint of smell and irritation to the skin.

The carboxyalkyl cellulose used as the water-soluble thickener is preferably one having a lower alkyl group in the alkyl moiety thereof, such as carboxymethyl cellulose or carboxyethyl cellulose, which is advantageous for the agent-fixing properties and the agent-releasability.

The polysaccharides as the water-soluble thickener include natural polysaccharides, such as pectin, gellan gum, glucomannan, guar gum, casein, and sodium alginate. Polysaccharides capable of crosslinking and gelling in the presence of polyvalent metal ions are also useful. The polyvalent metal ions include a calcium ion, a magnesium ion, a barium ion, a zinc ion, an iron ion, and an aluminum ion. Particularly preferred polysaccharides are pectin, casein, sodium alginate, gellan gum, and κ-carrageenan from the standpoint of the agent-fixing properties and the agent releasability.

Similarly to the first aspect, the agent is applied to at least the main absorbing region of the topsheet 2. While varying according to the kinds, the agent and the water-soluble thickener are preferably applied in a total amount of 0.1 to 20 g, particularly 0.5 to 15 g, especially 3 to 10 g, per $m^2$ of the main absorbing region of the topsheet 2, for obtaining as sufficient effects as is consistent with economy and for securing a good feel to the touch and absorbing performance.

The water-soluble thickener is preferably used in an amount of 5 to 100 parts by weight, particularly 10 to 50 parts by weight, per part by weight of the agent for securing sustainability of the agent while dry (i.e., controlling the transfer of the agent to the skin while dry) and releasability of the agent while wet.

The agent and the water-soluble thickener can be applied by, for example, uniformly mixing them with water and coating the topsheet 2 with the resulting aqueous solution or dispersion. Where the topsheet 2 is made of nonwoven fabric, the agent and the water-soluble thickener can previously be applied to fiber, from which the nonwoven fabric is fabricated.

In mixing the agent and the water-soluble thickener with water, the system can be heated up to a temperature higher than the water dissolving temperature of the thickener by about 20° C. thereby to accelerate dissolution of the agent and/or the thickener. Preferred concentrations of the agent and the water-soluble thickener in the aqueous solution or dispersion are 0.01 to 10% by weight, particularly 0.1 to 1% by weight, and 1 to 50% by weight, particularly 3 to 20% by weight, respectively. Within these concentration ranges, satisfactory drying efficiency is achieved; an extreme increase of viscosity of the aqueous solution or dispersion, which results in difficulty in uniform application, is avoided; and the aqueous solution or dispersion becomes uniform. As previously noted, the drying temperature of the aqueous solution or dispersion is preferably from room temperature up to 150° C., preferably from 50 to 80° C., in which range the thermal history of the agent can be kept mild. "Drying at room temperature" equals spontaneous drying.

The present invention is by no means limited to the aforesaid particular embodiments. In the first aspect of the invention, the skin-care agent may be fixed on a prescribed region of the diaper 1 in a state ready to be transferred to the wearer's skin and adhered thereto, as far as the skin-care agent is fixed in a state ready to be released therefrom on contact with water. Such a modification can be embodied by the following methods (i) to (v).

(i) The skin-care agent is applied to a portion where the elastic members 7 are disposed. An improved contact between the agent and the skin can be obtained, and the agent is physically transferred to the skin.

(ii) The skin-care agent is mixed with a substance which is liquid at ambient temperature and is substantially nonvolatile, such as 1,3-butylene glycol, glycerol, propylene glycol or squalane (they are known as humectants), or the above-described viscosity modifier, and the resulting composition having an increased viscosity is applied to the topsheet 2. The agent thus applied oozes out from the topsheet 2 when pressed while worn and adheres to the skin.

(iii) The skin-care agent is mixed with the aforementioned organic or inorganic particles to prepare a pasty or semi-solid composition, which is applied to the topsheet 2. On contact with the skin, the agent is transferred and adhered to the skin together with the particles.

(iv) Where the topsheet 2 is made of nonwoven fabric, the skin-care agent is previously added into the fiber before being fabricated into nonwoven fabric. The agent bleeds out on the surface of the fiber and is transferred and adhered to the skin.

(v) Porous powder, etc. is impregnated with the skin-care agent, and the impregnated powder is applied to the topsheet 2. The agent bleeds out on the surface of the porous powder and is transferred and adhered to the skin.

While the disposable diaper 1 according to the first and third aspects has the skin-care agent (or the agent having a prescribed effect on the skin) applied to the topsheet 2, which is a part of the skin-contacting surface (the inner surface of the diaper 1 which is to come into contact with the wearer's skin), the agent can be applied to the topsheet side of the absorbent member 4 instead of, or in addition to, the topsheet 2 by, for example, sprinkling the agent on the topsheet side of the absorbent member 4 to have a water activity of 0.7 or less.

In the third aspect in which the agent having a prescribed effect on the skin and the water-soluble thickener are applied to the topsheet 2, they can be applied to other portions of the skin-contacting surface, such as the cuffs made of nonwoven fabric, the leg portions, and the waist portions, instead of, or in addition to, the topsheet 2. In particular, when applied to the portions having elastic members, such as the leg portions and the waist portions, the agent is brought into sufficient contact with the skin by the elastic contraction of the elastic members and is thereby transferred to the skin effectively. In addition, scratches on the skin which may be caused by the tension of the elastic members can be alleviated.

The absorbent member 4 used in the first and third aspects can contain pulp as commonly employed in conventional diapers. The proportion of the superabsorbent polymer can be preferably 5 to 300 parts by weight per 100 parts by weight of pulp.

The particulars of the above-described embodiments are interchangeable.

The absorbent article according to the present invention is not limited to disposable diapers and includes sanitary napkins, incontinence pads, panty liners, and the like.

The present invention will now be illustrated in greater detail with reference to Examples, but it should be understood that the invention is not construed as being limited thereto. Unless otherwise noted, all the parts, percents, and ratios are by weight.

EXAMPLES 1 TO 3

Thirty parts of an ethanol extract of citron was used in Example 1. Similarly thirty parts of a 1,3-butylene glycol extract of hamamelis and a mixed extract comprising ethanol and 1,3-butylene glycol of hiba arborvitae were used in Examples 2 and 3, respectively. These plant extracts and 70 parts of a 5% aqueous solution of polyoxyethylene alkyl ether surfactant were mixed uniformly. The resulting mixture was applied to the entire surface of air-through nonwoven fabric made of eccentric core/sheath type conjugate fiber (2.2 dtex, 51 mm) having polypropylene as a core and polyethylene as a sheath to prepare a topsheet having the plant extract fixed thereto. The amount of the plant extract (the total amount of the active ingredient and the solvent) adhered was 0.15% based on the weight of the nonwoven fabric.

Separately, rayon fiber (1.7 dtex, 15 mm) and polyethylene terephthalate fiber (5.5 dtex, 51 mm) were mixed at a ratio of 30/70 to prepare air-through nonwoven fabric having a basis weight of 40 g/m². Superabsorbent polymer particles (crosslinked sodium polyacrylate; water absorption by centrifugal dewatering: 50 g/g) were scattered on the nonwoven fabric in an amount of 200 g/m². The resulting nonwoven fabric having the polymer particles held in the interstices of the constituting fibers was completely wrapped in tissue having a basis weight of 15 g/m² to prepare an absorbent member.

The topsheet was disposed on one side of the absorbent member, and a polyethylene film was disposed on the other side. Known fastening means, elastic members and the like were arranged to prepare a disposable diaper shown in FIG. 1.

EXAMPLE 4

A disposable diaper was prepared in the same manner as in Example 2, except that the air-through nonwoven fabric having the plant extract was subjected to embossing to make circular (diameter: 2 mm) bosses in an embossed area ratio of 25%.

COMPARATIVE EXAMPLE 1

One part of a 1,3-butylene glycol extract of bladder wrack and 2 parts of a 5% aqueous solution of polyoxyethylene alkyl ether surfactant were uniformly mixed. The mixture was applied to the surface of air-through nonwoven fabric made of core/sheath type conjugate fiber (2.2 dtex, 51 mm) having polypropylene as a core and polyethylene as a sheath to obtain a topsheet having the plant extract fixed thereto. The amount of the plant extract adhered was the same as in Example 1. A disposable diaper was prepared in the same manner as in Example 1, except for using the resulting topsheet.

COMPARATIVE EXAMPLE 2

A disposable diaper was prepared in the same manner as in Example 1, except that the plant extract was not applied to the air-through nonwoven fabric.
Evaluation of Performance Caregivers were asked to use the disposable diapers of Examples 1 to 4 and Comparative Examples 1 to 2 for 10 wearers for consecutive 2 weeks. The performance of the diapers was evaluated from whether or not a diaper rash developed and the degree of dissolution of the superabsorbent polymer and rated according to the following rating system. The results are shown in Table 1.
Rating System for Diaper Rash A . . . A diaper rash did not develop on 6 or more out of 10 wearers.

B . . . A diaper rash did not develop on 3 to 5 out of 10 wearers.

C . . . A diaper rash did not develop on one or two out of 10 wearers.

Rating System for Degree of Dissolution of Superabsorbent Polymer

A . . . Partly dissolved.

B . . . Dissolved by about half.

C . . . Almost dissolved.

TABLE 1

|  | Plant Extract | Diaper Rash | Dissolution of Superabsorbent Polymer |
|---|---|---|---|
| Example 1 | citron extract | A | A |
| Example 2 | hamamelis extract | A | A |
| Example 3 | *hiba arborvitae* extract | A | A |
| Example 4 | hamamelis extract | A | A |
| Compara. Example 1 | bladder wrack extract | B | B |
| Compara. Example 2 | — | B | A |

It is seen from the results in Table 1 that the disposable diapers according to the present invention are less causative of a diaper rash than the comparative diapers. It has also been proved that the dissolution of the superabsorbent polymer ascribed to the decomposition of the superabsorbent polymer is suppressed in the diapers of the present invention. While not shown in Table 1, the diapers of Examples felt dry with no stickiness.

EXAMPLE 5

One part of the agent shown in Table 2, 10 parts of polyvinyl alcohol (complete saponification product; degree of polymerization: 1700; water dissolving temperature: 60° C.), 90 parts of a textile oil (20% aqueous solution containing 30 parts of a sodium alkylphosphate and 70 parts of a polyoxyethylene alkyl ether sulfate as major components), and 900 parts of water were mixed at 80° C. to form an aqueous solution.

Core/sheath type conjugate fiber (3.3 dtex; 51 mm) having polypropylene as a core and polyethylene as a sheath was soaked in the aqueous solution. After taken out of the aqueous solution, the fiber was dried at 120° C. The fiber having the agent shown in Table 2 and polyvinyl alcohol adhered thereto was fabricated into air-through nonwoven fabric having a basis weight of 25 g/m². The hot air temperature in the production of the nonwoven fabric was 140° C. The resulting nonwoven fabric had 0.5 g/m² of the agent and 5 g/m² of polyvinyl alcohol uniformly adhered all over, which was used as a topsheet of a diaper.

A hundred parts of NBKP and 100 parts of superabsorbent polymer particles (crosslinked polyacrylic acid; water absorption by centrifugal dewatering: 50 g/g) were uniformly mixed. The mixture was wrapped in tissue having a basis weight of 15 g/m² to prepare an absorbent member having a total basis weight of 300 g/m².

The topsheet was disposed on one side of the absorbent member, and a polyethylene film was disposed on the other side. Known fastening means, elastic members and the like were arranged to prepare a disposable diaper shown in FIG. 1.

EXAMPLE 6

A disposable diaper was prepared in the same manner as in Example 5, except for using carboxymethyl cellulose (water dissolution temperature: 50° C.) in place of polyvinyl alcohol.

EXAMPLE 7

A disposable diaper was prepared in the same manner as in Example 5, except for using the agent shown in Table 2.

EXAMPLE 8

A disposable diaper was prepared in the same manner as in Example 5, except for using an aqueous dispersion prepared by adding 5 parts of nylon beads (average particle size: 3 μm) to the aqueous solution used in Example 5.

EXAMPLE 9

A disposable diaper was prepared in the same manner as in Example 5, except for using the agent shown in Table 2.

COMPARATIVE EXAMPLE 3

Polyolefin wax was used instead of polyvinyl alcohol. One part of the agent shown in Table 2, 100 parts of polyolefin wax, and 2 parts of a surfactant (polyoxyethylene (10 mol) adduct of hydrogenated castor oil) were preliminarily mixed and melted by heating at 80° C. to prepare a treating composition. A disposable diaper was prepared in the same manner as in Example 5, except that the topsheet was prepared by using the resulting treating composition.

Evaluation of Performance

The disposable diapers obtained in Examples 5 to 9 and Comparative Example 3 were evaluated for their performance in preventing liquid flow on the topsheet and preventing development of a diaper rash according to the following methods. The results of evaluation are shown in Table 2.

(1) Liquid Flow

The disposable diaper was fixed on a plate inclined at 45° with the topsheet up. Fifty grams of physiological saline was poured at a position 200 mm down from the upper edge of the diaper, and the distance the liquid flew on the topsheet was measured. The shorter the distance, the higher the properties of preventing liquid flow.

(2) Diaper Rash

Caregivers were asked to use the diaper for 15 wearers for consecutive 2 weeks, and development of a diaper rash was observed and rated as follows.

A . . . One or two out of 15 wearers experienced a diaper rash.

B . . . Three to seven out of 15 wearers experienced a diaper rash.

C . . . More than half of 15 wearers experienced a diaper rash.

TABLE 2

|  | Agent | Water-soluble Thickener | Liquid Flow (mm) | Diaper Rash |
|---|---|---|---|---|
| Example 5 | hamamelis extract | polyvinyl alcohol | 60 | A |
| Example 6 | hamamelis extract | carboxymethyl cellulose | 70 | A |
| Example 7 | hiba arborvitae extract | polyvinyl alcohol | 65 | A |
| Example 8 | hamamelis extract nylon beads | polyvinyl alcohol | 60 | A |
| Example 9 | bladder wrack extract | polyvinyl alcohol | 60 | A* |
| Comparative Example 3 | hamamelis extract | polyolefin wax | 150 | B |

*There was a case in which urine sometimes leaked when a diaper absorbed a large quantity of urine (250 to 300 g). The absorbent member of the diaper was disintegrated to find that part of the superabsorbent polymer had undergone decomposition.
Decomposition of the superabsorbent polymer was not observed in Examples 5 to 8, causing no leakage, even when the diapers absorbed a large amount of urine.

As is apparent from Table 2, liquid is less flowable on the surface of the topsheet of the disposable diapers according to the present invention than on the topsheet of the diaper of Comparative Example 3 having the plant extract fixed by a hydrophobic immobilizing agent (polyolefin wax). In Comparative Example 3, physiological saline flows on the polyolefin wax to a considerable degree. While not shown in Table 2, dissolution of the superabsorbent polymer due to decomposition was found suppressed in the diapers of Examples 5 to 9, especially Examples 5 to 8.

EXAMPLE 10

Ten parts of hamamelis extract (extracting solvent: 1,3-butylene glycol; available from Ichimaru Pharcos Co., Ltd.) and 90 parts of a textile oil (5% aqueous solution) comprising a sodium polyoxyethylene alkylphosphate, a potassium alkylphosphate, and sorbitan monostearate were mixed to prepare a solution. Core/sheath type conjugate fiber (3.3 dtex; 51 mm) having polypropylene as a core and polyethylene as a sheath was soaked in the solution. After taken out of the solution, the fiber was dried to obtain hamamelis extract-containing fiber. The amount of the skin-care agents including hamamelis and other agents adhered was 0.5% based on the hamamelis extract-containing fiber.

The resulting hamamelis extract-containing fiber was carded into a web, which was hot-air treated to obtain air-through nonwoven fabric having a basis weight of 30 g/m².

EXAMPLE 11

Hiba arborvitae extract-containing fiber and air-through nonwoven fabric made of the fiber were prepared in the same manner as in Example 10, except for replacing the hamamelis extract with hiba arborvitae extract (extracting solvent: 1,3-butylene glycol/ethanol mixture). The amount of the skin-care agents including hiba arborvitae and other agents adhered was 0.4% based on the hiba arborvitae extract-containing fiber.

EXAMPLE 12

Peach leave extract-containing fiber and air-through nonwoven fabric made of the fiber were prepared in the same manner as in Example 10, except for using 1 part of peach leave extract (powdered; available from Alps Kogyo K. K.) and 99 parts, in terms of the active ingredients, of the textile oil. The amount of the peach leave extract adhered was 0.2% based on the peach leave extract-containing fiber.

EXAMPLE 13

Thirty parts of hamamelis extract (extracting solvent: 1,3-butylene glycol; available from Ichimaru Pharcos Co., Ltd.) and 70 parts of a textile oil (5% aqueous solution)

comprising a sodium polyoxyethylene alkylphosphate, a potassium alkylphosphate, and sorbitan monostearate were mixed to prepare a solution. Core/sheath type conjugate fiber (3.3 dtex; 51 mm) having polypropylene as a core and polyethylene as a sheath was soaked in the solution. After taken out of the solution, the fiber was dried to obtain hamamelis extract-containing fiber A. The amount of the skin-care agents including hamamelis and other agents adhered was 0.5% based on the hamamelis extract-containing fiber A.

Separately, 10 parts of the same hamamelis extract as used above and 90 parts of a textile oil (5% aqueous solution) comprising a sodium alkylphosphate and a fatty acid diethanolamide were mixed to prepare a solution. Core/sheath type conjugate fiber (5.6 dtex; 51 mm) having polypropylene as a core and polyethylene as a sheath was soaked in the solution. After taken out of the solution, the fiber was dried to obtain hamamelis extract-containing fiber B. The amount of the skin-care agents including hamamelis and other agents adhered was 0.5% based on the hamamelis extract-containing fiber B.

The hamamelis extract-containing fibers A and B were separately carded into a web, and the resulting webs were superposed on each other and hot-air treated to obtain air-through nonwoven fabric having a double layer structure.

COMPARATIVE EXAMPLE 4

Core/sheath type conjugate fiber (5.5 dtex; 51 mm) having polypropylene as a core and polyethylene as a sheath was carded into a web, which was hot-air treated to obtain air-through nonwoven fabric. A mixture of 100 parts of polyolefin wax and 20 parts of isopropyl myristate was applied to the nonwoven fabric in an amount of 5 g/m² in a pattern of 100 mm-wide stripes at 10 mm intervals.

COMPARATIVE EXAMPLE 5

Sericin-containing fiber and air-through nonwoven fabric comprising the fiber were prepared in the same manner as in Example 12, except for replacing the peach leave extract with 1 part of sericin. The amount of sericin adhered was 2% based on the sericin-containing fiber.

Evaluation of Performance

The skin-care agent-containing fiber and nonwoven fabric obtained in Examples 10 to 13 and Comparative Examples 4 and 5 were evaluated for the water-solubility of the skin-care agent contained therein and their properties of inhibiting liquid from flowing thereon (initial flow distance), repeatedly absorbing liquid, and preventing development of a diaper rash according to the following methods. The results of evaluation are shown in Table 3.

(1) Water Solubility of Skin-Care Agent

The nonwoven fabric was soaked in 10 times as much water as its own weight at 25° C. The skin-care agent-releasability is "good" when the agent completely dissolved in water, or "poor" when the released agent made the water white turbid or formed a precipitate.

(2) Liquid Flow and Repeatedly Absorbing Performance

A hundred parts of NBKP and 100 parts of superabsorbent polymer particles (crosslinked polyacrylic acid; water absorption by centrifugal dewatering: 50 g/g) were uniformly mixed in an air stream and built up into a web on tissue having a basis weight of 20 g/m². The web was wrapped in the tissue to prepare an absorbent member having a total basis weight of 300 g/m². A disposable diaper was prepared by using the resulting absorbent member, the nonwoven fabric obtained in Examples 10 to 13 and Comparative Examples 4 to 5 as a topsheet, and a polyethylene film as a backsheet. In Example 13, the nonwoven fabric was placed on the backsheet in such a manner that the web comprising the hamamelis extract-containing fiber B faces the backsheet.

The disposable diaper was fixed on a plate inclined at 45° with the topsheet up. Fifty grams of physiological saline was poured at a position 200 mm from the upper end of the diaper three times, and the distance the liquid flew on the topsheet was measured after each pouring to obtain an average (initial flow distance).

Another 50 g portion of physiological saline was poured. The repeatedly absorbing properties of the nonwoven fabric were judged "good" when saline was absorbed smoothly, or "poor" when the flow distance exceeded 200 mm and saline leaked from the other end of the diaper.

(3) Diaper Rash

Caregivers were asked to use the diaper prepared above for 15 wearers for consecutive 2 weeks, and development of a diaper rash was observed and rated as follows.

A . . . One or two out of 15 wearers experienced a diaper rash.

B . . . Three to seven out of 15 wearers experienced a diaper rash.

C . . . More than half of 15 wearers experienced a diaper rash.

TABLE 3

| | Skin-Care Agent | Nonwoven fabric | Water Solubility of Agent | Initial Liquid Flow (mm) | Repeatedly Absorbing Performance | Prevention of Diaper Rash |
|---|---|---|---|---|---|---|
| Example 10 | hamamelis 1,3-butylene glycol | air-through (single layer) | good | 70 | good | A |
| Example 11 | hiba arborvitae 1,3-butylene glycol | air-through (single layer) | good | 75 | good | A |
| Example 12 | peach leave | air-through (single layer) | good | 85 | good | A |
| Example 13 | hamamelis 1,3-butylene glycol | air-through (double layer) | good | 60 | good | A |
| Comparative Example 4 | — | air-through (single layer) | poor | >200 | — | C |
| Comparative Example 5 | sericin | air-through (single layer) | poor | 120 | poor | B |

As is apparent from the results in Table 3, since the skin-care agent of the skin-care agent-containing fiber and nonwoven fabric according to the present invention has high water solubility, the nonwoven fabric is ready to release the skin-care agent into water to manifest high skin care effects. It has been proved that the skin-care agent fixed to the fiber causes no hindrance to the liquid permeation.

As fully described, the present invention provides an absorbent article having an superabsorbent polymer which effectively prevents development of a skin rash without accompanying impairment of the absorbing performance of the superabsorbent polymer.

The present invention also provides an absorbent article having a skin-care agent fixed thereto with reduced involvement of thermal history so that the agent keeps effective in suppressing or curing scratches, a rash or inflammation of wearer' skin.

The invention further provides skin-care agent-containing fiber and a fiber aggregate comprising the same, of which the skin-care agent has high water solubility to produce sufficiently high skin-care effects. The skin-care agent-containing fiber and the fiber aggregate can be produced by a simple process.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid retentive absorbent layer containing a superabsorbent polymer and liquid-impermeable leak proof layer, wherein an agent having a skin care effect and not causing a substantial reduction in water absorbing performance per unit weight of said superabsorbent polymer is fixed on a prescribed region of said absorbent article in a state ready to be released from that region on contact with moisture; an wherein said superabsorbent polymer has a water absorption of 30 g/g or more in terms of physiological saline absorption measured after centrifugal dewatering.

2. The absorbent article according to claim 1, wherein said agent is fixed on a skin-contacting surface of said absorbent article.

3. The absorbent article according to claim 1, wherein said agent comprises a water-soluble or water-dispersible plant extract.

4. An absorbent article comprising a liquid-permeable top layer, liquid impermeable leak proof layer and a liquid retentive absorbent layer interposed between said top layer and said leak proof layer, said absorbent layer containing a superabsorbent polymer, a main absorbing region in said top layer being provided with a skin-care composition consisting essentially of an agent which is released from said region, and dissolves or disburses in water upon contacting with a water content, said agent not causing substantial reduction in water absorbing performance per unit weight of said superabsorbent polymer; and wherein said superabsorbent polymer has a water absorption of 30 g/g or more in terms of physiological saline absorption measured after centrifugal dewatering.

5. An absorbent article comprising a liquid retentive absorbent layer and a liquid-impermeable leak proof layer, where an agent having a prescribed effect on the skin of a wearer and not causing a substantial reduction in water absorbing performance per unit weight of said absorbent layer is fixed with a water-soluble thickener on a prescribed region of said absorbent article; and wherein said superabsorbent polymer has a water absorption of 30 g/g or more in terms of physiological saline absorption measured after centrifugal dewatering.

6. The absorbent article according to claim 5, wherein said agent is fixed on a skin-contacting surface of said absorbent article.

7. The absorbent article according to claim 5, wherein said agent is fixed by applying an aqueous solution or dispersion of said agent and said water-soluble thickener to said prescribed region followed by drying.

8. The absorbent article according to claim 5, wherein said water-soluble thickener comprises polyvinyl alcohol, a carboxyalkyl cellulose, or a thickening polysaccharide.

9. The absorbent article according to claim 5, wherein said water-soluble thickener has a water dissolving temperature of 40 to 100° C.

10. An absorbent article comprising a liquid-permeable top layer, liquid impermeable leak proof layer and a liquid retentive absorbent layer interposed between said top layer and said leak proof layer, said absorbent layer containing a superabsorbent polymer, a main absorbing region in said top layer being provided with a skin-care composition consisting essentially of an agent which is released from said region, and dissolves or disburses in water upon contacting with a water content, and a water-soluble thickener which fixes said agent on said region, said agent not causing a substantial reduction in water absorbing performance per unit weight of said superabsorbent polymer; and wherein said superabsorbent polymer has a water absorption of 30 g/g or more in terms of physiological saline absorption measured after centrifugal dewatering.

* * * * *